United States Patent [19]

Becker et al.

[11] 4,271,076

[45] Jun. 2, 1981

[54] TRICYCLIC LACTONES

[75] Inventors: Joseph J. Becker, Geneva; Günther Ohloff, Bernex, both of Switzerland

[73] Assignee: Firmenich, S.A., Geneva, Switzerland

[21] Appl. No.: 168,149

[22] Filed: Jul. 14, 1980

[30] Foreign Application Priority Data

Aug. 31, 1979 [CH] Switzerland .......................... 7899/79

[51] Int. Cl.$^3$ ........................................... C07D 311/74
[52] U.S. Cl. ............................ 260/343.21; 252/522 R; 426/536; 131/277; 424/279
[58] Field of Search ..................................... 260/343.21

[56] References Cited

U.S. PATENT DOCUMENTS

| 3,981,892 | 9/1976 | Skorianetz | 260/343.21 |
| 4,159,258 | 6/1979 | Ohloff et al. | 260/343.21 |

OTHER PUBLICATIONS

Mueller et al., Chem. Abst. 27174w, vol. 69, 1968.

*Primary Examiner*—Henry R. Jiles
*Assistant Examiner*—Jane T. Fan
*Attorney, Agent, or Firm*—Scully, Scott, Murphy & Presser

[57] ABSTRACT

New tricyclic lactones, viz. 10,10-dimethyl-3-oxa[7.1.1.0$^{2,7}$]undec-2(7)-en-4-one and 10,10-dimethyl-3-oxa-tricyclo[7.1.1.0$^{2,7}$]undec-4-one. These latter are useful perfuming and flavor-modifying ingredients.

3 Claims, No Drawings

TRICYCLIC LACTONES

BRIEF SUMMARY OF THE INVENTION

The invention relates to the field of perfumery and of the flavour industry, in particular it relates to novel tricyclic lactones having the formula

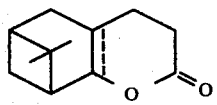

possessing a single or a double bond in the position indicated by the dotted line, as well as the use thereof as perfuming or flavour-modifying ingredients. The invention further relates to a perfume or flavour composition containing said lactones as active ingredients.

BACKGROUND OF THE INVENTION

In the perfumery as well as in the flavour industry, a lot of efforts are devoted today to the replacement of expensive naturally occurring raw materials or the reproduction of original organoleptic effects by making use of new chemicals. Among the numerous synthetic odorants prepared in a recent past, bi-, tri- or polycyclic derivatives of decalin can be cited as examples, as well as bicyclo[2.2.1]heptane, bicyclo[2.2.2]octane, cedrene or caryophyllene derivatives.

For instance, the tricyclic compound of formula

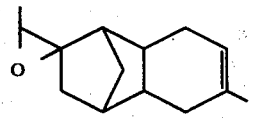

is appreciated in the art for its original floral and woody odour—see e.g. Swiss Pat. No. 547 850—as well as the compound of formula

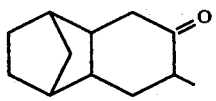

which is used in perfumery for developing or enhancing woody and spicy odour notes—see e.g. Swiss Pat. No. 557 870—. As further example of tricyclic fragrant compounds, one can also cite the compound of formula

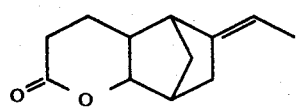

characterized by its original odour note, at the same time sweet, fresh, spicy and herbaceous—see e.g. DE-OS No. 28 26 302.

Notwithstanding the relative abundance of tricyclic fragrant compounds known in the art, there still remains a constant need of enrichment of the palette of the perfumer, or of the flavourist, by the finding of new active substances.

PREFERRED EMBODIMENTS OF THE INVENTION

We have surprisingly found that the tricyclic lactones of the invention, viz. 10,10-dimethyl-3-oxatricyclo[7.1.1.0$^{2,7}$]undec-2(7)-en-4-one and 10,10-dimethyl-3-oxa-tricyclo[7.1.1.0$^{2,7}$]undecan-4-one, are particularly useful ingredients for preparing both perfumes and flavour compositions.

In the field of perfumery, the compounds of formula (I) are characterized by their sweet, herb-like and slightly spicy note, reminiscent of that of tobacco, honey and tonka beans. The said compounds can thus be widely used in modern perfumery, for example as perfuming ingredients for the preparation of fruity, spicy, lactonic or "fougère" compositions to which they advantageously confer elegance and harmony. The compounds of formula (I) are also suitable for preparing perfumed articles such as soaps, detergents, household materials or cosmetic products, lotions, shampoos or beauty creams for example.

The proportions of compounds of formula (I) to be used for the achievement of the above cited olfactive effects may vary within a wide range and are more generally comprised between about 1 and 20 weight percent of the weight of the considered composition. Proportions higher or lower than those given above may also be used, depending on the particular effect which is desired. It must be added that 10,10-dimethyl-3-oxatricyclo[7.1.1.0$^{2,7}$]undec-2(7)-en-4-one is the preferred perfuming ingredient of the invention.

In the field of flavours, the compounds of formula (I) may be defined as possessing a taste and aroma of sweet, flowery, woody, herbal and coumarin type. They can thus advantageously be used for the preparation of various artificial flavours such as caramel, nut, coconut, honey or cocoa flavours, as well as flavours of the fruity type, cherry flavours e.g. The said compounds can also be used for flavouring foodstuffs, feedstuffs, beverages, pharmaceutical preparations or tobacco products.

The proportions to be used for the achievement of the above mentioned gustative effects are generally comprised between about 1 and 1000 ppm (parts per million) of the weight of the flavoured material. In the case of the aromatization of tobacco products, said proportions are more particularly comprised between about 100 and 200 ppm. However, higher or lower proportions than those given hereinabove can also be used, especially when more particular effects are desired. It must be added that 10,10-dimethyl-3-oxa-tricyclo[7.1.1.0$^{2,7}$]undec-2(7)-en-4-one is the preferred flavouring ingredient.

10,10-Dimethyl-3-oxa-tricyclo[7.1.1.0$^{2,7}$]undec-2(7)-en-4-one and 10,10-dimethyl-3-oxa-tricyclo[7.1.1.0$^{2,7}$]undecan-4-one, which are both novel compounds, can be easily prepared according to the usual techniques, by making use of 2-carbethoxy-nopinone as starting material as illustrated hereinbelow:

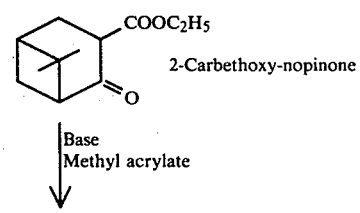
2-Carbethoxy-nopinone

Base
Methyl acrylate

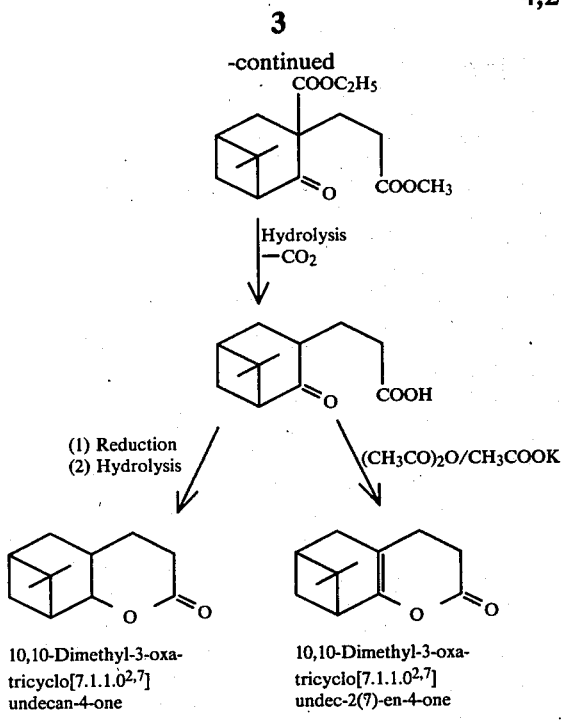

10,10-Dimethyl-3-oxa-tricyclo[7.1.1.0²,⁷]undecan-4-one 10,10-Dimethyl-3-oxa-tricyclo[7.1.1.0²,⁷]undec-2(7)-en-4-one 2-Carbethoxy-nopinone used hereinabove as starting material can easily be prepared from β-pinene, after transformation thereof into nopinone and subsequent carbethoxylation. The detail of the preparation of the new compounds of the invention is given in the following examples (temperatures in degrees centigrade).

EXAMPLE 1

10-10-Dimethyl-3-oxa-tricyclo[7.1.1.0²,⁷]undec-2(7)-en-4-on (a) 420 g (2.0 M) of 2-carbethoxy-nopinone were first heated to 40° in the presence of 200 ml of methyl alcohol and 0.4 g of hydroquinone. 206 g (2.4 M) of methyl acrylate were then added to the above mixture, over a period of about 1 hour. The reaction mixture was stirred for 30 minutes at 45°, then cooled to room temperature, neutralized with 40 ml of acetic acid and finally diluted with 200 ml of water. After extraction by means of 800 ml of toluene, washing of the organic layer with water, drying over $Na_2SO_4$ and fractional distillation, there were isolated 502 g (85% yield) of a compound having b.p. 100°–145°/0.1 Torr and identified as

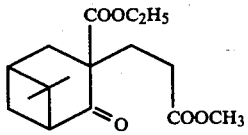

according to the following analysis.

IR: 2950, 1755, 1725–1710 cm$^{-1}$

NMR: 0.96 (3H, s); 1.30 (2H, t); 1.38 (3H, s); 1.8–2,4 (4H, m); 2.46 (3H, s); 2.50–2.95 (4H, m); 3.68 (3H, s); 4,26 (2H, qd) δ ppm MS: m/e=138(8), 122(18), 107(24), 95(27), 87(76), 67(26), 55(52), 41(100)

(b) 617 g (2.08 M) of the above diester in 1500 ml of water were heated during 6 h at 80°, in the presence of 700 ml of NaOH 30% in water. After cooling to room temperature, the reaction mixture was poured into 3000 ml of water and 450 g of concentrated $H_2SO_4$. After extraction by means of 2000 ml of toluene, washing with water (1000 ml), drying over $Na_2SO_4$ and evaporation, there were obtained 468 g of crude material. After drying at 50° during 2 h, there were finally isolated 310 g (71% yield) of 3-(4,4-dimethyl-2-oxo-bicyclo[3.1.1]heptyl)-propionic acid.

An analytical sample was purified by means of recristallization in a 1:1 mixture of petroleum ether (b.p. 80°–100°) and toluene, m.p. 90°–93°.

IR: 3000, 1720 cm$^{-1}$

NMR: 0.76 (3H, s); 1.35 (3H, s); 1.5–2.8 (several m); 10.4 (broad s) δ ppm (c) 42 g (0.2 M) of the above crude keto-acid were stirred during 6 h at room temperature, in the presence of 2 g of potassium acetate in 100 ml of acetic anhydride. After evaporation of the volatile parts under reduced pressure (10 Torr), the obtained residue was then subjected to high vacuum distillation to afford 15 g of unreacted starting material and 18 g (47% yield) of the desired compound, having b.p. 85°–95°/0.05 Torr.

NMR: 0.86 (3H, s); 1.35 (3H, s+1H, d); 2.10–2.85 (9H, several m) δ ppm

MS: M$^+$=192(25); m/e=177(6), 149(39), 135(9), 121 (12), 107(10), 95(14), 85(23), 67(9), 55(100), 41(23)

2-Carbethoxy-nopinone used hereinabove as starting material was prepared as follows: 324 g (6.0 M) of sodium methoxide were progressively added to a mixture of 414 g (3.0 M) of nopinone—see Rec. Trav. Chim. Pays-Bas 90, 1034 (1971)—, 1880 g (16 M) of ethyl carbonate and 20 ml of anhydrous ethyl alcohol (addition period: 20 minutes-temperature: 20°–30°). The reaction mixture was heated during 7 h at 50°, then 9 h at 70° and finally kept overnight at room temperature. After having been poured into a mixture of 600 ml of acetic acid and 2500 ml of water, the reaction mixture was extracted with ethyl acetate (1500 ml). After washing of the organic layer with water, drying over $Na_2SO_4$, evaporation and final distillation through a VIGREUX column, there were isolated 482 g (77% yield) of the desired compound, having b.p. 70°–82°/0.1 Torr.

EXAMPLE 2

10,10-Dimethyl-3-oxa-tricyclo[7.1.1.0²,⁷]undecan-4-one 3.8 g (0.1 M) of sodium borohydride were added in small portions to a mixture of 50 g (0.24 M) of 3-(4,4-dimethyl-2-oxo-bicyclo[3.1.1]heptyl)-propionic acid—see Example 1, letter b)—, 42.5 g of sodium hydroxide 35% in water and 375 ml of water (addition period: 2 h—temperature: 25°). After having been stirred for 3 h at room temperature, the reaction mixture was heated at 50° during 8 h, then cooled to 30° and finally poured into 90 ml of $H_2SO_4$ 25% in water. After further heating at 80° for 15 minutes and cooling to room temperature, the reaction mixture was extracted by means of 1500 ml of toluene. After washing of the organic layer with water, drying over $Na_2SO_4$ and fractional distillation, there were isolated 13 g (28% yield) of the desired compound, having b.p. 110°–114°/0.05 Torr.

An analytical sample was purified by recristallization in ethyl alcohol, m.p. 57°–60°.

NMR: 0.94 (3H, s); 1.22 (3H, s+1H, d); 1.48–2.75 (10H, several m); 4.75 (1H, qd) δ ppm MS: M$^+$=194(40); m/e=179(20), 166(27), 151(18), 133(40), 121(42), 105(58), 94(89), 81(100), 79(75), 67(36), 55(65), 41(90)

EXAMPLE 3

A base perfume composition for a masculine "Eau de toilette" was prepared as indicated hereinafter.

| Ingredients | Parts by weight |
| --- | --- |
| Bergamot oil | 240 |
| VETYRISIA ®[1] | 200 |
| Lavender oil 48/50 | 60 |
| Lemon oil (terpeneless) | 50 |
| Treated birch tar oil 10%* | 50 |
| Galbanum oil 10%* | 50 |
| Hydroxycitronellal[2] | 30 |
| Rosemary oil | 30 |
| Neroli bigarade oil | 20 |
| Geranium Bourbon oil | 20 |
| Incense resinoid 50%* | 20 |
| Oak moss absolute (discolourized) 50%* | 20 |
| Levo-citronellol | 20 |
| FIXATEUR 404[3] 10%* | 20 |
| Nutmeg oil | 15 |
| Cubeba oil | 5 |
| Total | 850 |

*in diethyl phthalate
[1]origin: FIRMENICH SA
[2]CYCLOSIA BASE ® (FIRMENICH SA)
[3]origin: FIRMENICH SA (see S. Arctander, Perfume and Flavor Chemicals, Montclair NJ 1969, Section 1391)

The above base composition, which is characterized by a pleasant leathery, spicy and woody odour, is particularly suitable for preparing masculine cosmetic preparations such as "Eau de toilette" or after-shave lotions e.g.

By adding 15 parts of 10,10-dimethyl-3-oxa-tricyclo[7.1.1.0$^{2,7}$]undec-2(7)-en-4-one to 85 parts of the above base, there was obtained a new perfume composition having a dominating spicy note, the overall odour of which was qualified as more elegant and more harmonious than that of the said base.

An analogous olfactive effect was observed when, in the above example, 10,10-dimethyl-3-oxa-tricyclo [7.1.1.0$^{2,7}$ undec-2(7)-en-4-one as replaced by 10,10-dimethyl-3-oxa-tricyclo[7.1.1.0$^{2,7}$]undecan-4-one. In this latter case however, 30 parts of the said compound were added to 70 parts of the above base composition.

EXAMPLE 4

The two following beverages were flavoured with 10,10-dimethyl-3-oxa-tricyclo[7.1.1.0$^{2,7}$]undec-2(7)-en-4-one as indicated hereinafter (dosage):
(a) commercial pasteurized milk (2.5 ppm)
(b) commercial cherry juice (3.0 ppm).

The thus flavoured (test) samples were then subjected to organoleptic evaluation by comparison with an unflavoured (control) material. The results of the said evaluation are summarized as follows:
(a) enhanced sweet note, slightly caramel-like
(b) more intense sweet and fruity taste.

An analogous, but less marked, olfactive effect was observed when, in the above example, 10,10-dimethyl-3-oxa-tricyclo[7.1.1.0$^{2,7}$]undec-2(7)-en-4-one was replaced by 10,10-dimethyl-3-oxa-tricyclo[7.1.1.0$^{2,7}$]undecan-4-one.

EXAMPLE 5

1.5 g of a 1% solution of 10,10-dimethyl-3-oxa-tricyclo[7.1.1.0$^{2,7}$ undec-2(7)-en-4-one in 95% ethyl alcohol were sprayed onto 100 g of a mixture of tobacco of "american blend" type. The tobacco thus flavoured was used to manufacture test cigarettes which were then subjected to organoleptic evaluation by comparison with non-flavoured cigarettes (control). The tobacco used to manufacture the control cigarettes was preliminary treated with 95% ethyl alcohol.

The results of such an evaluation are summarized hereinafter:
1. odour of tobacco before smoking: herbal note, typical tobacco odour more intense than that of the control sample
2. taste and aroma of cigarettes smoke: sweet, herbal effect of coumaric type, more pronounced than that of the control sample.

An analogous, but less marked, olfactive effect was observed when, in the above example, 10,10-dimethyl-3-oxa-tricyclo[7.1.1.0$^{2,7}$]undec-2(7)-en-4-one was replaced by 10,10-dimethyl-3-oxa-tricyclo[7.1.1.0$^{2,7}$]undecan-4-one.

What we claim is:
1. A compound of the formula

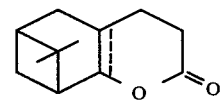

(I)

possessing a single or a double bond in the position indicated by the dotted line.

2. 10,10-Dimethyl-3-oxa-tricyclo[7.1.1.0$^{2,7}$]undec-2(7)-en-4-one.

3. 10,10-Dimethyl-3-oxa-tricyclo[7.1.1.0$^{2,7}$]undecan-4-one.

* * * * *